US00PP16884P3

(12) United States Plant Patent
Koot

(10) Patent No.: US PP16,884 P3
(45) Date of Patent: Jul. 25, 2006

(54) ***SKIMMIA* PLANT NAMED 'MAGIC MARLOT'**

(50) Latin Name: *Skimmia japonica*
Varietal Denomination: Magic Marlot

(76) Inventor: Jim Koot, Dongenseweg 3A, 5171 NA, Kaatsheuvel (NL)

( * ) Notice: Subject to any disclaimer, the term of this patent is extended or adjusted under 35 U.S.C. 154(b) by 41 days.

(21) Appl. No.: 10/973,883

(22) Filed: Oct. 26, 2004

(65) Prior Publication Data

US 2005/0155124 P1 Jul. 14, 2005

(30) Foreign Application Priority Data

Dec. 31, 2003 (EP) ..... 20032522

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—Mark P. Bourgeois

(57) ABSTRACT

A new cultivar of *Skimmia* plant named 'Magic Marlot' that is characterized by variegated foliage with young leaves that have yellow margins, mature leaves that have cream colored margins and flower buds that start as cream colored during the summer changing to bronze in autumn and to dark pinkish red in the winter.

1 Drawing Sheet

Botanical classification: *Skimmia japonica.*
Variety denomination: 'Magic Marlot'.

BACKGROUND OF THE INVENTION

The present invention relates to a new and distinct cultivar of *Skimmia* plant botanically known as *Skimmia japonica* and hereinafter referred to by the cultivar name 'Magic Marlot'.

'Magic Marlot' was discovered in the Summer of 1998 as a naturally occurring branch mutation on a plant of *Skimmia japonica* 'Marlot' (not patented). The cultivar 'Magic Marlot' was discovered in a cultivated area of Kaatsheuvel, The Netherlands.

Asexual reproduction by softwood cuttings of the new cultivar 'Magic Marlot' first occurred in the Summer of 1998 in Kaatsheuvel, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Skimmia* cultivar 'Magic Marlot'. These traits in combination distinguish 'Magic Marlot' as a new and distinct cultivar.

1. *Skimmia* 'Magic Marlot' exhibits flower buds that start as cream colored during the summer and change to bronze in autumn and to dark pinkish red in the winter.
2. *Skimmia* 'Magic Marlot' exhibits variegated foliage with young leaves that have yellow margins and mature leaves that have cream colored margins.

The closest comparison cultivar is the parent plant *Skimmia* 'Marlot'. The new cultivar 'Magic Marlot' is distinguishable from the parent *Skimmia* 'Marlot' by the following characteristics:

1. *Skimmia* 'Magic Marlot' has flower buds that start as cream colored during the summer and change to bronze in autumn and to dark pinkish red in the winter. The flower buds of 'Marlot' are green during the summer and change to bronze during the fall and winter.
2. *Skimmia* 'Magic Marlot' has variegated foliage with young leaves that have yellow margins and mature leaves that have cream colored margins. The leaves of 'Marlot' are green.

BRIEF DESCRIPTION OF THE DRAWINGS

The accompanying photographs illustrate the distinguishing traits of *Skimmia* 'Magic Marlot'.

The top photograph shows an overall view of a 1 year old plant.

The bottom photograph shows a close-up view of the leaves and flowers. The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Skimmia* cultivar named 'Magic Marlot'. Data was collected in Kaatsheuvel, The Netherlands from 1 year old plastic greenhouse grown plants in 15 cm. diameter containers. The time of year was April and the temperature averaged 15° Centigrade during the day and 7° Centigrade night. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species.

'Magic Marlot' has not been tested under all possible conditions and phenotypic differences may be observed with variations in environmental, climatic, and cultural conditions, however, without any variance in genotype.

Botanical classification: *Skimmia* 'Magic Marlot'.
Use: Ornamental. Perennial.
Parentage: 'Magic Marlot' is a naturally occurring branch mutation of *Skimmia japonica* 'Marlot'.
Vigor: Low.
Growth habit: Broad Upright.
Plant shape: Broad inverted triangle.
Suitable container size: 15 cm. container.
Height: 11 cm. in height.
Width: 17 cm. in width.
Hardiness: USDA Zone 7.
Propagation: Softwood cuttings.
Time to initiate roots: Approximately 35 days to produce roots on an initial cutting.
Time to produce a rooted cutting or liner: Approximately 85 days.
Crop time: From a softwood cutting, approximately 14 months are required to produce a finished plant.
Root system: Fine and fibrous.
Stem:
- *Branching habit.*—Free branching.
- *Average number of lateral branches.*—6.
- *Pinching.*—Yes.
- *Lateral branch diameter.*—3 mm. in diameter.
- *Lateral branch length.*—5.7 cm. in length.
- *Lateral branch strength.*—Strong.
- *Stem color.*—143A to 143B.
- *Pubescence.*—Absent.
- *Internode length.*—Average 7 mm. between nodes.
- *Shape.*—Round.
- *Surface.*—Glabrous, dull.

Foliage:
- *Texture.*—Smooth.
- *Leaf arrangement.*—Alternate.
- *Compound or single.*—Single.
- *Quantity of leaves per lateral branch.*—6.
- *Leaf shape.*—Narrow Elliptic to oblanceolate.
- *Leaf apex.*—Apiculate.
- *Leaf base.*—Attenuate.
- *Leaf length.*—4.7 cm. in length.
- *Leaf width.*—1.5 cm. in width.
- *Pubescence.*—Absent.
- *Leaf margin.*—Entire.
- *Vein pattern.*—Pinnate.
- *Young leaf color* (*lower surface*).—143C with margins 154D.
- *Young leaf color* (*upper surface*).—Between 143B and 144A with margins 154D.
- *Mature leaf color* (*lower surface*).—138B with blotches 157C, margins 154D.
- *Mature leaf color* (*upper surface*).—189A with blotches 188B, margins 150D to 157A.
- *Vein color* (*lower surface*).—143A.
- *Vein color* (*upper surface*).—189A.
- *Leaf attachment.*—Petiolate.
- *Petiole dimensions.*—3 mm. in length and 2 mm. in width.
- *Petiole color.*—145D.
- *Durability of foliage to stress.*—Moderate to high.

Inflorescence:
- *Inflorescence arrangement.*—Terminal paniculate thyrse.
- *Inflorescence type.*—Thyrse.
- *Inflorescence height.*—4.7 cm. in height.
- *Inflorescence width.*—4.3 cm. in width.
- *Quantity of flowers per inflorescence.*—Approximately 400.
- *Flowering habit.*—Annually.
- *Quantity of flowers per lateral stem.*—Approximately 400.
- *Quantity of flower buds per lateral stem.*—Approximately 400.
- *Quantity of flowers and buds per plant.*—Approximately 2400.
- *Flowering season.*—Late winter.
- *Rate of flower opening.*—Approximately 30% of the flowers are opened at once.
- *Time to flower.*—10 months.
- *Fragrance.*—Moderately strong, pleasant.
- *Flower bud length.*—2 mm. in length.
- *Flower bud diameter.*—1.5 mm. in diameter.
- *Flower bud shape.*—Broad oval to short obovate.
- *Bud color.*—Between 181A and 185B.
- *Rate of bud opening.*—3 weeks.
- *Flower aspect.*—Outward.
- *Flower shape.*—Cruciate.
- *Flower dimensions.*—7 mm. in diameter and 5 mm. in height.
- *Flower longevity.*—Lasts approximately 8 days on plant.
- *Petal appearance.*—Dull, slightly velvety.
- *Petal texture.*—Smooth.
- *Petal arrangement.*—Cruciate.
- *Number of petals.*—Four in number.
- *Petals fused or unfused.*—Unfused.
- *Petal shape.*—Obovate.
- *Petal margin.*—Entire.
- *Petal apex.*—Rounded.
- *Petal base.*—Cuneate.
- *Petal dimensions.*—3.5 mm. in length, 1.5 mm. in width.
- *Petal color when opening* (*upper side*).—White, N155A.
- *Petal color when opening* (*under side*).—White, N155A.
- *Petal color fully open* (*upper side*).—White, N155A.
- *Petal color fully open* (*under side*).—White, N155A.
- *Petal color fading to.*—Not fading.
- *Self-cleaning or persistent.*—Self-cleaning.

Sepals:
- *Sepal arrangement.*—Cruciate.
- *Sepal color immature* (*upper side*).—182C to 182D.
- *Sepal color immature* (*under side*).—182C to 182D.
- *Sepal color mature* (*upper side*).—145C to 145D.
- *Sepal color mature* (*under side*).—145C to 145D.
- *Sepal surface.*—Smooth, dull.
- *Number of sepals.*—Four.
- *Sepal shape.*—Broad elliptic.
- *Sepal margin.*—Entire.
- *Sepal apex.*—Broad acute.
- *Sepal base.*—Cuneate.
- *Sepal dimensions.*—1 mm. in length and 1 mm. in width.

Calyx:
- *Calyx shape.*—Cruciate.

*Calyx dimensions.*—1 mm. in length and 2 mm. in diameter.

Peduncle:

*Peduncle dimensions.*—3.7 cm. in length and 2 mm. in diameter.

*Peduncle color.*—143A to 143B.

*Peduncle strength.*—Moderate.

Pedicels:

*Pedicel dimensions.*—2 mm. in length and 0.7 mm. in diameter.

*Pedicel color.*—145C to 145D.

*Pedicel strength.*—Weak.

Reproduction organs:

*Stamen number.*—4.

*Anther shape.*—Dorsifixed, broad kidney-shaped and flattened.

*Anther dimensions.*—0.8 mm. in length.

*Anther color.*—162A to 162B.

*Amount of pollen.*—Low.

*Pollen color.*—13A to 13B.

*Ovary color.*—145A to 145B.

Seed: Seed production has not been observed.

Disease and pest resistance: Plants of the new *Skimmia* have not been observed for disease or pest resistance.

It is claimed:

1. A new and distinct variety of *Skimmia* plant named 'Magic Marlot' as described and illustrated.

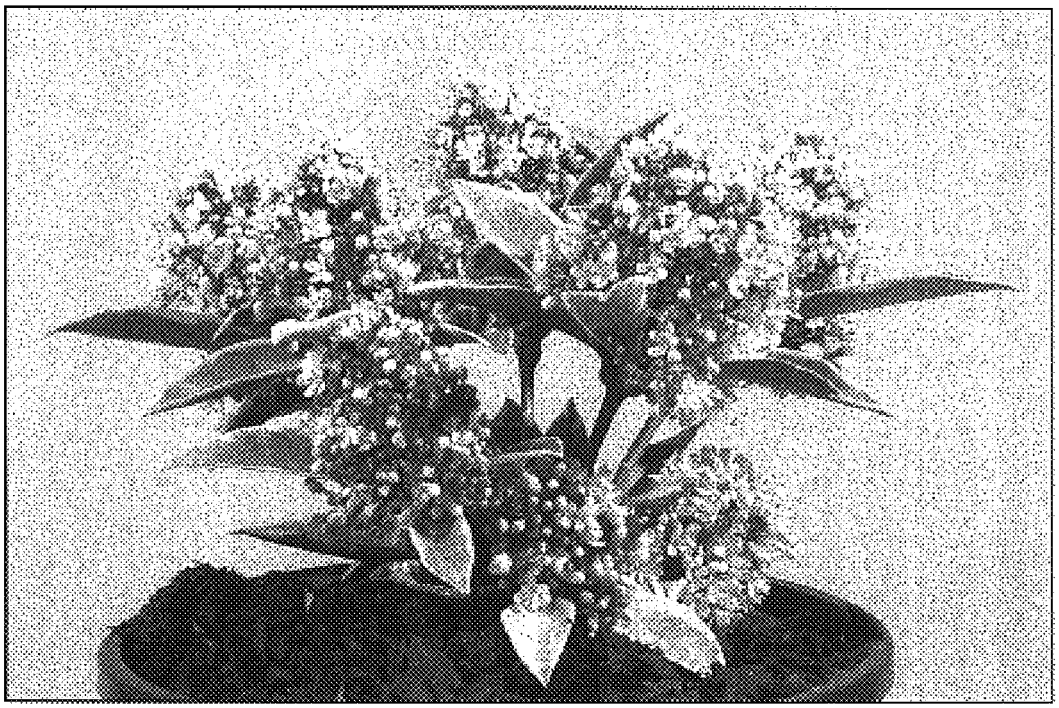
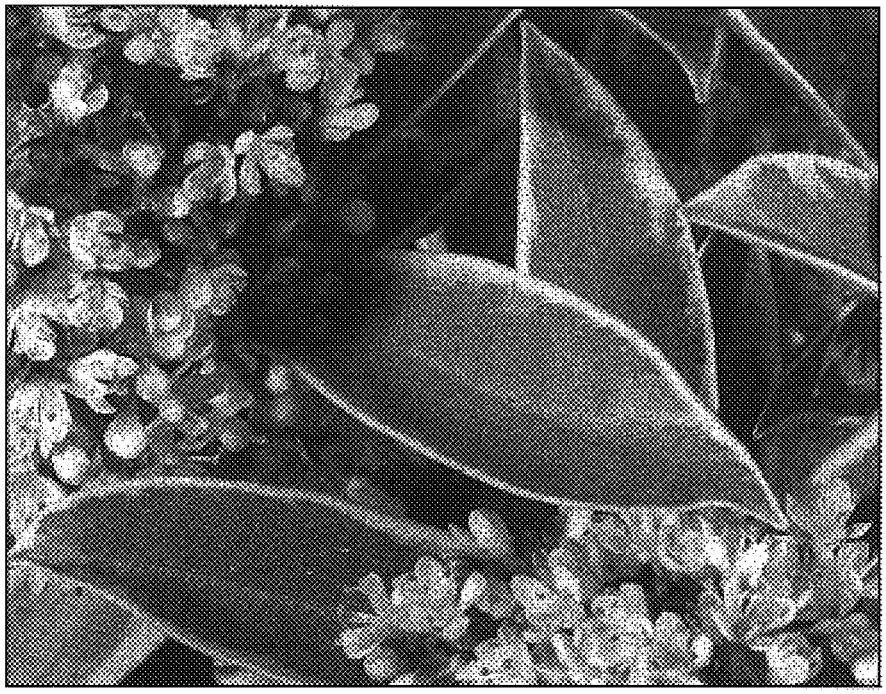

* * * * *